(12) United States Patent
Kubota et al.

(10) Patent No.: US 9,541,526 B2
(45) Date of Patent: Jan. 10, 2017

(54) NON-DESTRUCTIVE TESTING DEVICE FOR TESTING A WELDED REGION OF A WORKPIECE

(75) Inventors: Toshihiko Kubota, Tokyo (JP); Osamu Kawanabe, Tokyo (JP); Takashi Kimura, Aichi (JP); Atsushi Okuda, Aichi (JP)

(73) Assignees: Honda Motor Co., Ltd., Tokyo (JP); Nippon Kouatsu Electric Co., Ltd., Aichi (JP)

( * ) Notice: Subject to any disclaimer, the term of this patent is extended or adjusted under 35 U.S.C. 154(b) by 403 days.

(21) Appl. No.: 14/110,768

(22) PCT Filed: Apr. 5, 2012

(86) PCT No.: PCT/JP2012/059366
§ 371 (c)(1),
(2), (4) Date: Nov. 4, 2013

(87) PCT Pub. No.: WO2012/141074
PCT Pub. Date: Oct. 18, 2012

(65) Prior Publication Data
US 2014/0049254 A1    Feb. 20, 2014

(30) Foreign Application Priority Data

Apr. 12, 2011    (JP) .................................. 2011-088520

(51) Int. Cl.
*G01N 27/72*    (2006.01)
*G01B 7/12*    (2006.01)
(Continued)

(52) U.S. Cl.
CPC ............... *G01N 27/72* (2013.01); *G01B 7/003* (2013.01); *G01B 7/12* (2013.01); *G01N 27/902* (2013.01)

(58) Field of Classification Search
CPC .... G01N 27/82; G01N 27/72; G01N 27/9046; G01B 7/003; G01B 7/12; B23K 11/248; B23K 20/121; B23K 9/091; B23Q 35/13; G05F 7/00
See application file for complete search history.

(56) References Cited

U.S. PATENT DOCUMENTS

| 5,747,989 A * | 5/1998 | Kimura ............. G01N 27/9013 324/235 |
| 6,232,774 B1 | 5/2001 | Kimura |

(Continued)

FOREIGN PATENT DOCUMENTS

JP    H10-26609 A    1/1998
JP    3098193 B2    10/2000
(Continued)

OTHER PUBLICATIONS

Notice of Reasons for Rejection issued to JP Application No. 2013-509868, mailed Oct. 22, 2013.
(Continued)

*Primary Examiner* — Vinh Nguyen
(74) *Attorney, Agent, or Firm* — Carrier Blackman & Associates, P.C.; William D. Blackman; Fulchand P. Shende

(57) ABSTRACT

The device has a processor (20) that applies a magnetic field to a measurement subject (2) and after the magnetic field is discontinued, uses an induced electromotive force detector (17) to measure the magnetic fluxes emitted from multiple locations, calculates time constants of transient change of the plurality of magnetic fluxes, and detects the internal structure of the measurement subject (2) from the distribution of the time constants. The processor (20) prompts the induced electromotive force detector (17) to make first measurements at predetermined locations, prompts the induced electromotive force detector (17) to make second measurements at locations rotated by a predetermined angle from the predetermined locations, and based on the internal structure detected by the first measurements and the internal structure detected by the second measurements, estimates the center location of the nugget and/or the diameter of the (Continued)

nugget which has been formed inside the measurement subject (2).

9 Claims, 13 Drawing Sheets

(51) Int. Cl.
    *G01N 27/90*     (2006.01)
    *G01B 7/00*     (2006.01)

(56) References Cited

U.S. PATENT DOCUMENTS 6,683,452 B2 * 1/2004 Lee ................. G01N 27/82
    324/220
7,109,702 B2 * 9/2006 Imamoto ............ G01N 27/9046
    324/240

2005/0122099 A1     6/2005 Imamoto et al.

FOREIGN PATENT DOCUMENTS

| JP | 2001-324396 A | 11/2001 |
| JP | 2001-324479 A | 11/2001 |
| JP | 2005-345307 A1 | 12/2005 |
| JP | 2009-063441 A | 3/2009 |
| WO | 03/027661 A1 | 4/2003 |
| WO | 2010/146939 A1 | 12/2010 |

OTHER PUBLICATIONS

Extended European Search Report issued Aug. 21, 2014 in the corresponding EP Patent Application 12770758.6.
Keiji Tsukada et al., "A magnetic flux leakage method using a magnetoresistive sensor for nondestructive evaluation of spot welds", NDT&E International 44 (2011) pp. 101-105.

* cited by examiner

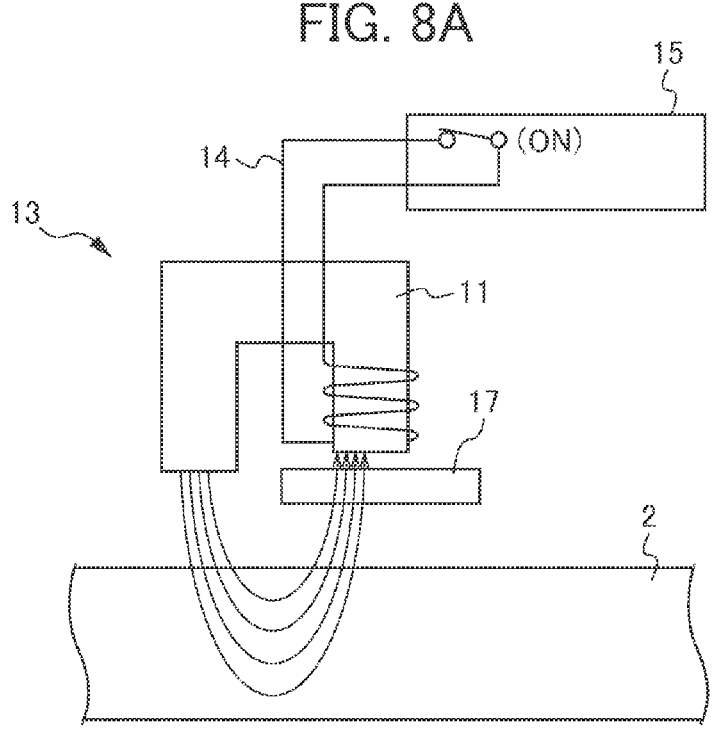
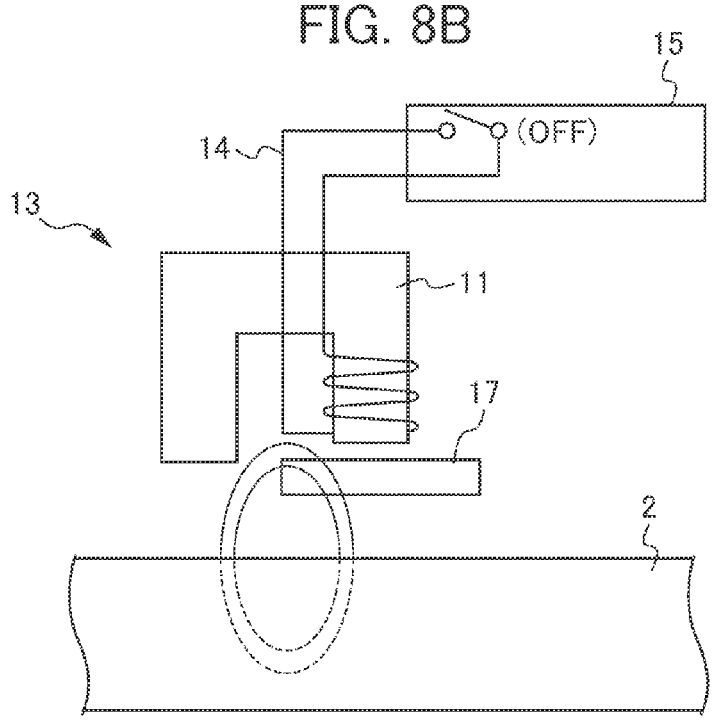

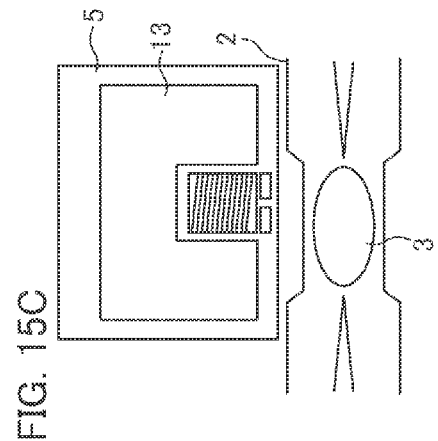 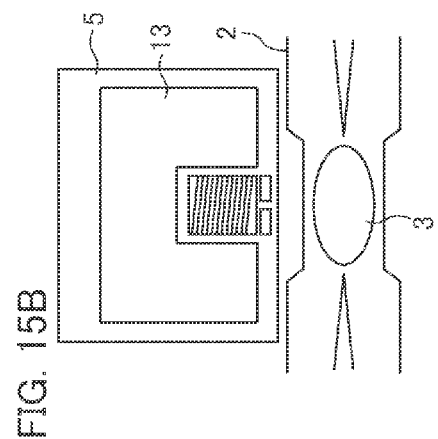 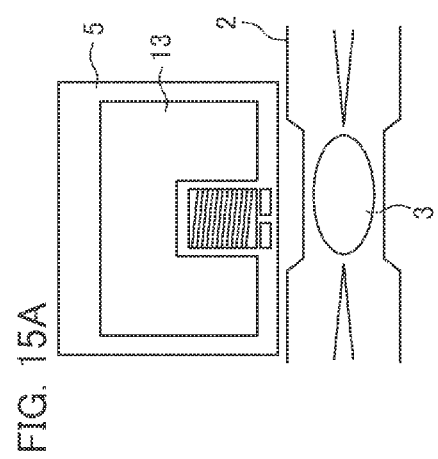
 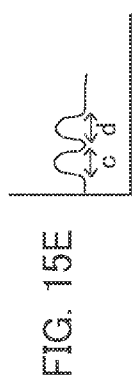 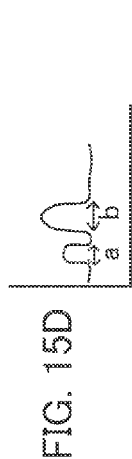
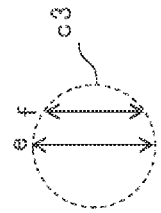 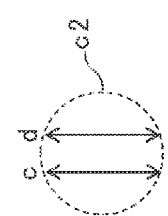 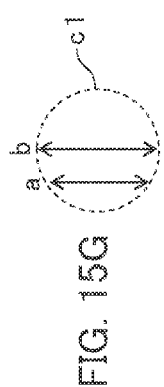
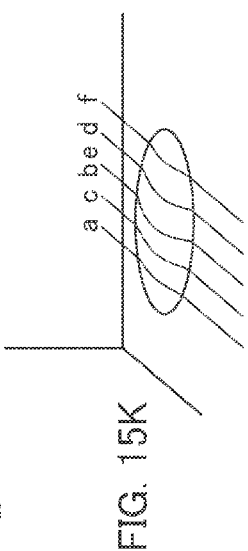 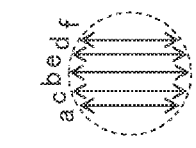

NON-DESTRUCTIVE TESTING DEVICE FOR TESTING A WELDED REGION OF A WORKPIECE

TECHNICAL FIELD

The present invention relates to a non-destructive testing device that tests a welded region or the like of a measurement subject.

BACKGROUND ART

Spot welding has been commonly employed as the welding used in the construction of various thin plate metallic products. Spot welding is a method of welding that interposes a welded region of overlapped metal plates from above and below by electrodes having leading ends molded into a predetermined shape, at a predetermined pressure, and flows a predetermined current between both electrodes for a predetermined time, thereby locally heating the welded region and welding.

In addition, the surface of the welded region welded by way of spot welding is indented compared to outside of the welded part due to the pressure. This concaved part is referred to as an indentation, and the dimension of the concaved part is referred to as indentation diameter.

In addition, inside of the welded region is formed by a nugget (weld) and a crimp at the periphery thereof. The nugget is a portion at which the metal temporary melted and solidified. On the other hand, the crimp is a portion pressure bonded at the surfaces of the metal. The dimension of the nugget is referred to as nugget diameter, the nugget and crimp are collectively referred to as a joint, and the dimension of the joint is referred to as joint diameter. It should be noted that the joint is actually the joined portion.

In addition, since the overlapped metal plates are welded at a point (spot) in spot welding, it is necessary to test whether or not the weld strength is sufficient.

As a method of performing measurement of the weld strength non-destructively, a method of estimating the weld strength by measuring the nugget diameter is effective (for example, refer to Patent Document 1). Conventionally, as a method of measuring the nugget diameter, a method has been known that applies to the welded region a magnetic field generated by coils through which current flows, and then obtains the nugget diameter from the change in inductance of the coils generated as a result thereof. With the conventional method, since there is a property whereby the magnetic permeability ($\mu$) changes between the nugget and portions other than the nugget, the change in magnetic permeability ($\mu$) is detected as the change in inductance using this property, whereby the nugget diameter is obtained.

Patent Document 1: Japanese Patent Publication No. 3098193

DISCLOSURE OF THE INVENTION

Problems to be Solved by the Invention

Herein, the sensor of the testing device is approximately arranged at a welded region that can be confirmed by sight externally. However, the center location of the concaved part (indentation) that can be confirmed by sight externally, and the center location of the nugget may not match. This occurs in a case like the leading ends of the electrodes not strictly opposing each other upon spot welding, but rather opposing each other at a certain angle.

When the center location of the welded region and the center location of the nugget are displaced in this way, it is not possible to accurately measure the nugget diameter since the nugget is not formed, or is displaced from, directly under where the sensor of the testing device is arranged. In such a case, the sensor of the testing device must be shifted to various position and retesting repeated, and thus a great amount of labor is required in the measurement of nugget diameter.

In addition, in a case of fixing the testing device to a robot arm and performing automated measurement, offset with the workpiece (measurement subject) becomes a problem. Herein, a system has been considered that performs alignment by attaching a camera or the like to a robot arm, and detecting a welding dent or a color change in the workpiece during welding.

However, as mentioned above, there is no guarantee that the position of the welding dent and the position of the nugget will match, and it is difficult to automatically make the testing device be arranged at the center location of the nugget.

The present invention has been made taking the aforementioned such issues into account, and one object thereof is to provide a non-destructive testing device that can perform testing of a welded region such as the center location of a nugget and nugget diameter efficiently, without using a mechanism to perform alignment such as a camera.

Means for Solving the Problems

In order to solve the above-mentioned problem, a non-destructive testing device according to the present invention is a configuration that includes a detection processor that causes a magnetic flux density to be generated by applying a magnetic field to a measurement subject, measures magnetic flux emitted from a plurality of locations on the measurement subject by way of a magnetic flux detection element, after the magnetic field is discontinued, calculates a plurality of time constants of transient change in magnetic flux, and detects an internal structure of the measurement subject from a distribution state of the time constants, in which the detection processor performs a first measurement at a first location of the measurement subject using the magnetic flux detection element, performs a second measurement at a second location, and estimates a center location of a nugget formed inside of the measurement subject and/or diameter of the nugget based at least on an internal structure detected by the first measurement and an internal structure detected by the second measurement.

In order to solve the above-mentioned problem, a non-destructive testing device according to the present invention is a configuration that includes a detection processor that causes a magnetic flux density to be generated by applying a magnetic field to a measurement subject, measures magnetic flux emitted from a plurality of locations on the measurement subject by way of a magnetic flux detection element, after the magnetic field is discontinued, calculates a plurality of time constants of transient change in magnetic flux, and detects an internal structure of the measurement subject from a distribution state of the time constants, in which the detection processor performs a first measurement at a predetermined location of the measurement subject using the magnetic flux detection element, performs a second measurement at a location rotated a predetermined angle from the predetermined location of the measurement subject using the magnetic flux detection element, and estimates a center location of a nugget formed inside of the measurement subject and/or diameter of the nugget based on an internal structure detected by the first measurement and an internal structure detected by the second measurement.

In addition, the non-destructive testing device may be a configuration in which the magnetic flux detection element includes a plurality of microcoils arranged in a row, and the detection processor performs the first measurement by arranging the magnetic flux detection element at a predetermined location on the measurement subject, and performs the second measurement by arranging the magnetic flux detection element at a location rotated by a predetermined angle from the predetermined location on the measurement subject.

Furthermore, the non-destructive testing device may be a configuration in which the magnetic flux detection element includes a plurality of microcoils arranged in one vertical line and one horizontal line in a cross shape, and the detection processor arranges the magnetic flux detection element at a predetermined location on the measurement subject, performs the first measurement by way of the magnetic flux detection element arranged in the one vertical line or one horizontal line, and performs the second measurement by way of the magnetic flux detection element arranged in the one horizontal line or one vertical line.

In order to solve the above-mentioned problem, a non-destructive testing device according to the present invention is a configuration that includes a detection processor that causes a magnetic flux density to be generated by applying a magnetic field to a measurement subject, measures magnetic flux emitted from a plurality of locations on the measurement subject by way of a magnetic flux detection element, after the magnetic field is discontinued, calculates a plurality of time constants of transient change in magnetic flux, and detects an internal structure of the measurement subject from a distribution state of the time constants, in which magnetic recovery portions are provided in a longitudinal direction of an excitation portion in parallel on both sides thereof, and a plurality of magnetic flux detection elements is arranged below the excitation portion so as to correspond to the magnetic recovery portions, and in which the detection processor measures, by way of the plurality of magnetic flux detection elements, a magnetic flux emitted from a plurality of locations on the measurement subject, and estimates a center location of a nugget formed inside of the measurement subject and/or a diameter of the nugget, based on results of the measurement.

In addition, the non-destructive testing device may be a configuration in which the magnetic flux detection element includes a first magnetic flux detection element and a second magnetic flux detection element, the first magnetic flux detection element is arranged below the excitation portion in parallel to one magnetic recovery portion, the second magnetic flux detection element is arranged below the excitation portion in parallel to another magnetic recovery portion, and the detection processor acquires measurement results of the first magnetic flux detection element and the second magnetic flux detection element, forms a triangle by extracting from the measurement results three points that are the most distant, forms a circumscribed circle passing through the three points from an intersection of perpendicular bisectors on the triangle arrived at by respectively calculating perpendicular bisectors of two sides forming the triangle, and calculates a center location and diameter of the circumscribed circle, thereby estimating a center location of a nugget formed inside of the measurement subject and/or a diameter of the nugget.

Furthermore, the non-destructive testing device may be a configuration including an arm portion that holds a measurement device having the magnetic flux detection element; and a drive controller that moves the arm portion so that the magnetic flux detection element is arranged at a predetermined location on the measurement subject serving as a measurement target.

Moreover, the non-destructive testing device may be a configuration including a display unit; and a display controller that controls the display unit, in which the display controller generates a virtual image of the nugget based on the center location and/or diameter of the nugget, in a case of the center location of the nugget formed inside of the measurement subject and/or the diameter of the nugget having been estimated, and displays the virtual image on the display unit.

Effects of the Invention

According to the present invention, it is possible to efficiently find the center location of a nugget and perform testing of a welded region.

BRIEF DESCRIPTION OF THE DRAWINGS

FIG. 8A and FIG. 8B provides views schematically showing an aspect of when applying a magnetic field to cause magnetic flux density to be generated;

FIG. 15A to FIG. 15K provides views offering an explanation for the flow of processing when displaying a virtual image of a nugget.

Figure 1:
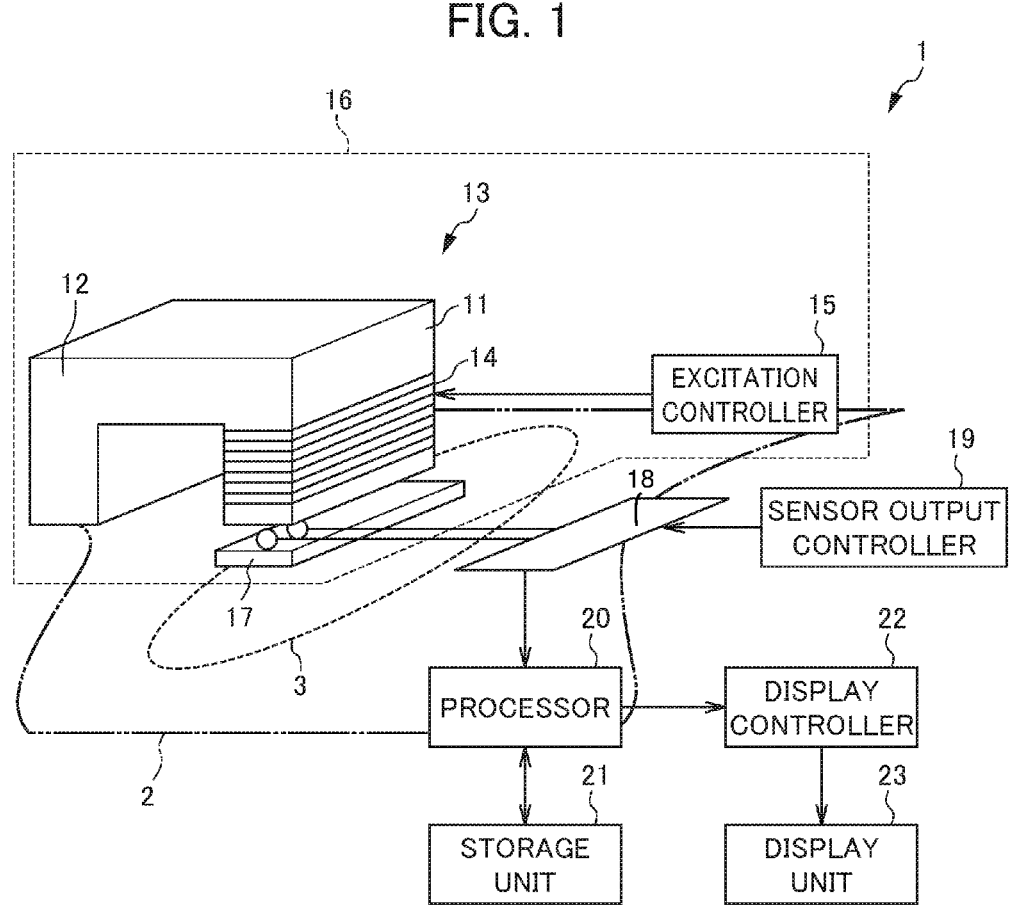
FIG. 1 is a block diagram showing the configuration of a non-destructive testing device according to the present embodiment.

EXPLANATION OF REFERENCE NUMERALS 1 non-destructive testing device
2 measurement subject
5 sensor probe
11 excitation pole
12 common pole
13 magnetic core
14 exciting coil
15 excitation controller
16 magnetic flux generator
17 induced electromotive force detector (magnetic flux detection element)
18 sensor output switch
19 sensor output controller
20 processor (detection processor)
21 storage unit
22 display controller
23 display unit

PREFERRED MODE FOR CARRYING OUT THE INVENTION

Spot welding is a method of melting at least two parts to make integrated. A device that performs spot welding passes high current for a short time to weld parts, while interposing and strongly pressurizing two metal plates between rod electrodes of pure copper or copper alloy. In addition, slight depressions made by pinning with the electrodes are formed in the surface of the welded region, and inside thereof, a nugget is formed (part at which weld metal solidified). A non-destructive testing device 1 according to the present embodiment tests the nugget non-destructively. It should be noted that testing of the welded region welded by way of spot welding will be explained in the present example; however, the welding method is not limited to spot welding. In addition, "inner structure" indicates the structure that is changing chemically, physically and mechanically.

Moreover, the non-destructive testing device 1 is a device that performs testing on a welded area 3 of a measurement subject 2 (e.g., body of a vehicle) configured from a magnetic substance, and employs a non-destructive testing method that applies a magnetic field to the welded area 3, and estimates the presence or absence of a nugget, center location of the nugget and diameter by measuring the magnetic flux density emitted. Hereinafter, an embodiment of the present invention will be explained.

As shown in FIG. 1, the non-destructive testing device 1 includes a magnetic flux generator 16, induced electromotive force detector 17 (magnetic flux detection element), sensor output switch 18, sensor output controller 19, processor 20 (detection processor), and storage unit 21. The magnetic flux generator 16 has a magnetic core 13 configured from an excitation pole 11 and a common pole 12, an exciting coil 14 that excites the magnetic core 13, and an excitation controller 15 that controls the energized state and isolated state of the exciting coil 14.

Herein, the form of the magnetic core 13 will be explained. As schematically shown in FIG. 1, the magnetic core 13 is formed in a substantially U-shape in which the excitation pole 11 is formed on one end side and the common pole 12 is formed on the other end side. In addition, coils C1 to Cn (n being a natural number of not less than 2) formed at the end face of the excitation pole 11 detect the change in magnetic flux occurring in the welded area 3. It should be noted that the form of the magnetic core 13 is not limited to the aforementioned form.

In addition, the magnetic flux generator 16 causes a magnetic flux to be generated between the excitation pole 11 and common pole 12 by controlling the exciting coil 14 the energized state by way of the excitation controller 15, thereby applying a magnetic field to the welded area 3. The exciting coil 14 is formed by a solenoid coil in which a conductor is wound tightly in a helical pattern at a predetermined part of the magnetic core 13. It should be noted that, although one in which the exciting coil 14 is wound is explained as the excitation pole 11 in the present example, since one in which the exciting coil 14 is wound becomes the excitation pole or becomes the common pole depending on the direction of current flowing in the exciting coil 14, one in which the exciting coil 14 is wound may be established as the common pole.

In addition, the induced electromotive force detector 17 is disposed at the end face of the excitation pole 11, and detects a change in magnetic flux occurring in the welded area 3. Moreover, the induced electromotive force detector 17 is configured by an array coil in which a plurality of coils C is arranged.

Figure 2:
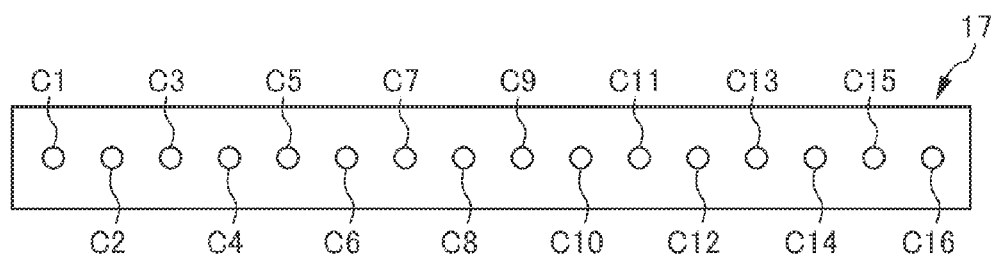
FIG. 2 is a view showing the configuration of an induced electromotive force detector of the non-destructive testing device according to the present embodiment.

Furthermore, the induced electromotive force detector 17 has a plurality of microcoils arranged in axial symmetry, as shown in FIG. 2. FIG. 2 shows an aspect of 16 coils (C1 to C16) being arranged uniformly in the induced electromotive force detector 17. More specifically, coil C1 and coil C16; coil C2 and coil C15, coil C3 and coil C14; coil C4 and coil C13; coil C5 and coil C12; coil C6 and coil C11; coil C7 and coil C10; and coil C8 and coil C9 are arranged uniformly so as to be in axial symmetry, respectively. It should be noted that, although the microcoils are explained in the present embodiment as being configured in a row of 16, it is not limited thereto, and may be configured by a plurality of coils in a plurality of lines.

In addition, the welded marks (hereinafter referred to as welding dents) can be confirmed by sight in the surface of the welded area 3. In the testing by the non-destructive testing device 1, a magnetic flux density is generated by applying a magnetic field to the surface of this welding dent, and testing of the weld state is performed inside thereof by way of the coils C1 to C16.

In addition, the sensor output controller 19 sequentially selects the outputs from the plurality of coils C1 to C16 included in the array coil. The sensor output switch 18 outputs a signal from a coil C selected by the sensor output controller 19 to the processor 20.

The processor 20 calculates a decay time constant $\tau_1$ of the magnetic energy and the decay time constant $\tau_2$ of the eddy-current loss, based on the signals supplied from the sensor output switch 18. Although the details are described later, the distribution of the decay time constant $\tau_1$ of the magnetic energy of the nugget is measured, and when this is analyzed, it is possible to obtain the form and dimensions of a portion in which a compositional change occurs metallically like a nugget.

The processor 20 performs a first measurement with the induced electromotive force detector 17 at a first location of the measurement subject 2, and performs a second measurement at a second location, then estimates the center location of a nugget formed inside of the measurement subject 2 and/or the diameter of the nugget, based at least on the inner structure detected by the first measurement and the inner structure detected by the second measurement.

More specifically, the processor 20 performs the first measurement with the induced electromotive force detector 17 at a predetermined location on the measurement subject 2 (for example, welded area 3 that can be confirmed visually from outside, or at the periphery thereof), subsequently performs the second measurement at a location rotated a predetermined angle (for example, 90°) from the predetermined location on the measurement subject 2 with the induced electromotive force detector 17, and estimates the center location of the nugget formed inside of the measurement subject 2 and the diameter of the nugget, based on the inner structure detected by the first measurement and the inner structure detected by the second measurement.

Herein, the principle will be explained for estimating the center location of the nugget formed inside of the measurement subject 2 and the diameter of the nugget based on the inner structure detected by the first measurement and the inner structure detected by the second measurement by way of the processor 20. It should be noted that, hereinafter, an explanation will be provided assuming that the nugget is circular form.

In the first and second measurements, in the case of the central part of the detection (sensor) surface of the induced electromotive force detector 17 (for example, between the coil C8 and coil C9 in FIG. 2) overlapping the same location in the vertical direction with the central part of the nugget (case of being concentric), the central coordinates $(x_0, y_0)$ of the nugget become $(0,0)$. In other words, $x_0=y_0=0$.

Figure 3:
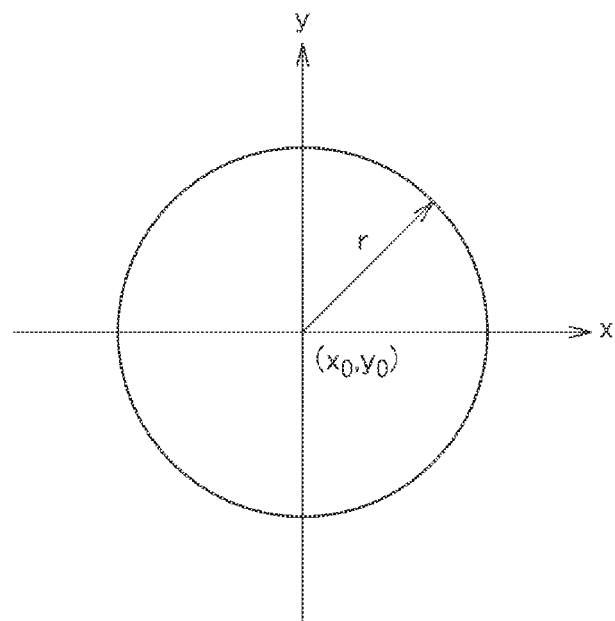
FIG. 3 is a view offering an explanation for a case of the induced electromotive force detector and the center of a nugget being concentric.

In addition, since the distance between coils C of the induced electromotive force detector 17 is known beforehand, it is possible to calculate the diameter of the nugget (radius r in the present example) based on the inner structure (refer to FIG. 3). Moreover, when the nugget is assumed to be circular form, the radius r becomes the same in the x direction and y direction.

Furthermore, in the first and second measurement, in a case of the central part of the detection (sensor) surface of the induced electromotive force detector 17 (for example, between the coil C8 and coil C9 in FIG. 2) being at different locations in the vertical direction with the central part of the nugget, the central coordinates $(x_0, y_0)$ of the nugget are calculated in accordance with the following formulas (1) and (2).

$$X_0 = (x_1 + x_2)/2 \quad (1)$$

$$Y_0 = (y_1 + y_2)/2 \quad (2)$$

In addition, the diameters in the x direction and y direction are calculated in accordance with the following formulas (3) and (4), respectively.

[Math. 1]

$$|x| = x_2 - x_1 \quad (3)$$

$$|y| = y_2 - y_1 \quad (4)$$

Moreover, letting the radius be r, the size in the x direction of the nugget is calculated as follows.
[Math. 2]

$$(x - x_0)^2 + (y - y_0)^2 = r^2$$

Herein, x is calculated as follows from the solution of the formula.

$$x = x_0 \pm \sqrt{r^2 - (y - y_0)^2}$$

In addition, the intercept $|X|$ of x is calculated as follows.

$$|x| = \left(x_0 + \sqrt{r^2 - (y - y_0)^2}\right) - \left(x_0 - \sqrt{r^2 - (y - y_0)^2}\right)$$

$$= 2\sqrt{r^2 - (y - y_0)^2}$$

In addition, $r^2$ is calculated by squaring both sides.

$$|x|^2 = 4(r^2 - (y - y_0)^2)$$

$$r^2 = \frac{|x|^2}{4} + (y - y_0)^2$$

Herein, since $x_1$ and $x_2$ are both $y=0$, $r_x$ in the x direction is calculated as follows.

$$r_x^2 = \frac{|x|^2}{4} + y_0^2 \therefore \quad (5)$$

$$r_x = \sqrt{\frac{|x|^2}{4} + y_0^2}$$

In addition, $r_y$ in the y direction is similarly calculated as follows.

$$r_y^2 = \frac{|y|^2}{4} + x_0^2 \therefore \quad (6)$$

$$r_y = \sqrt{\frac{|y|^2}{4} + x_0^2}$$

The processor 20 calculates the radius $r_2$ of the nugget by substituting $r_x$ and $r_y$ into the following formula (7) and calculating the average value in the x direction and y direction.

[Math. 3]

$$r_2 = \frac{r_x + r_y}{2} \quad (7)$$

Therefore, in the first measurement, the processor 20 detects $x_1$ and $x_2$ based on the detection value detected from the induced electromotive force detector 17, substitutes into formula (1), calculates $x_0$, substitutes into formula (3), and then calculates the diameter in the x direction.

In addition, in the second measurement, the processor 20 detects $y_1$ and $y_2$ based on the detection value detected from the induced electromotive force detector 17, substitutes into formula (2), calculates $y_0$, and substitutes into formula (4), and then calculates the diameter in the y direction.

Next, the processor 20 calculates $r_x$ by substituting the diameter in the x direction and $y_0$ into formula (5), and calculates $r_y$ by substituting the diameter in the y direction and $x_0$ into formula (6). Then, the processor 20 substitutes $r_x$ and $r_y$ into formula (7), and calculates the diameter $r_2$ of the nugget. In other words, in view of the foregoing, it will be understood that the detection processor 20 is adapted to estimate a center location $(x_0, y_0)$ of a nugget (c) formed inside of the measurement subject 2 and/or diameter of the nugget (c), by calculating an intersection between: a perpendicular line passing through a central point of a connecting line of first two points ($x_1$, $x_2$) extracted, by acquiring measurement results from the first measurement, and extracting from the measurement results of the first two points ($x_1$, $x_2$) corresponding to two microcoils ($mcx_1$, $mcx_2$) of the first subset of microcoils, the first two points ($x_1$, $x_2$) corresponding to a contour line of the nugget (c); and a perpendicular line passing through a central point of a connecting line of second two points ($y_1$, $y_2$) extracted, by acquiring measurement results from the second measurement, and extracting from the measurement results of the second two points ($y_1$, $y_2$) corresponding to two microcoils ($mcy_1$, $mcy_2$) of the second subset of microcoils, the second two points ($y_1$, $y_2$) corresponding to the contour line of the nugget (c); setting the intersection thus calculated as a center location ($x_0$, $y_0$), and calculating a diameter of a circle passing through the first two points ($x_1$, $x_2$) or the second two points ($y_1$, $y_2$) centering around the center location ($x_0$, $y_0$).

Figure 4:
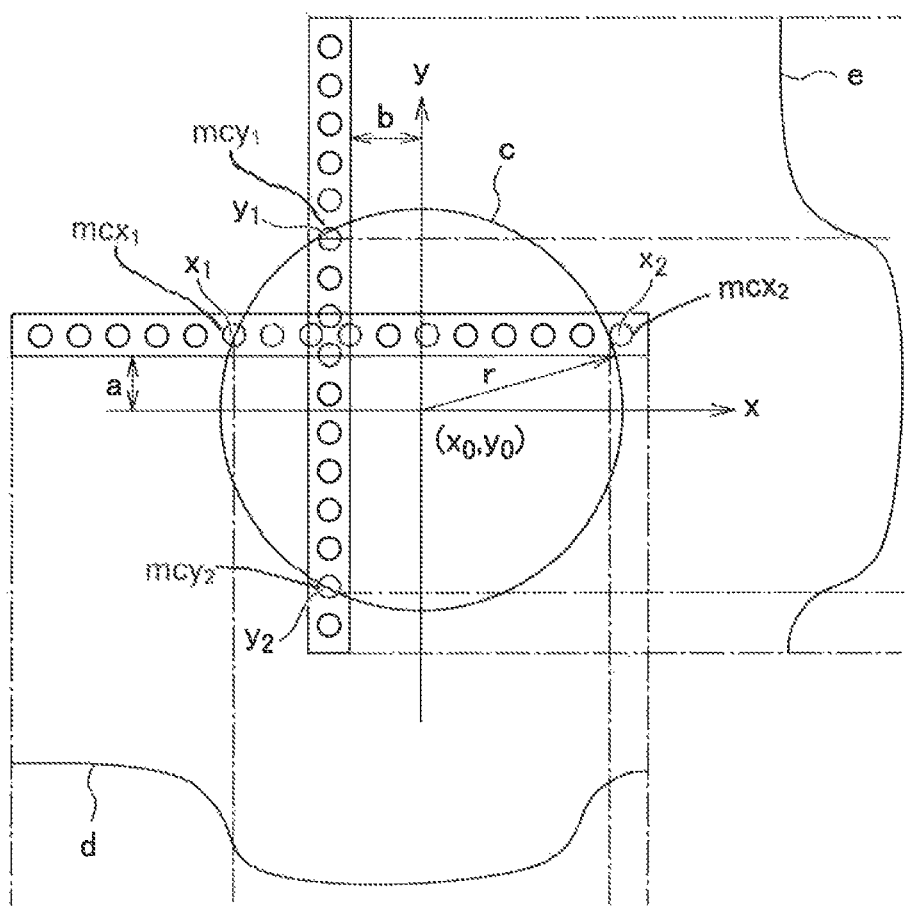
FIG. 4 is a view offering an explanation for a case of the induced electromotive force detector and the center of the nugget being displaced.

In this way, the non-destructive testing device 1 has detection (sensor) surfaces of the induced electromotive force detector 17 made in the shape of a cross as shown in FIG. 4, and can detect deviation from the center location of the nugget (deviation of x axis defined as deviation b, and deviation of y axis defined as deviation a), when repeating the first measurement and second measurement. In other words, the non-destructive testing device 1 can measure the center location of the nugget and diameter of the nugget, based on the deviation from the central portion of the nugget (c in FIG. 4), by way of measurement of the same location differing by 90°. In addition, as shown in FIG. 4, with the non-destructive testing device 1, in the case of the detection surface of the induced electromotive force detector 17 being displaced from the central portion of the nugget, the result of the first measurement (measurement in x-axis direction) becomes the waveform as shown by d in FIG. 4, and the result of the second measurement (measurement in y-axis direction) becomes the waveform as shown by e in FIG. 4.

Next, a case of the microcoils configuring the induced electromotive force detector 17 being arranged in a row, and a case of the microcoils being arranged length and width wise in a cross shape will be explained.

Case of Microcoils Arranged in a Row

The induced electromotive force detector 17 may be configured by a plurality of microcoils being arranged in a row. In a case of being configured in this way, the processor 20 performs the first measurement, arranging the induced electromotive force detector 17 at a predetermined location on the measurement subject 2, and subsequently, performs the second measurement, arranging the induced electromotive force detector 17 at a location rotated from the predetermined location on the measurement subject 2 by a predetermined angle (for example, 90°).

Figure 5:
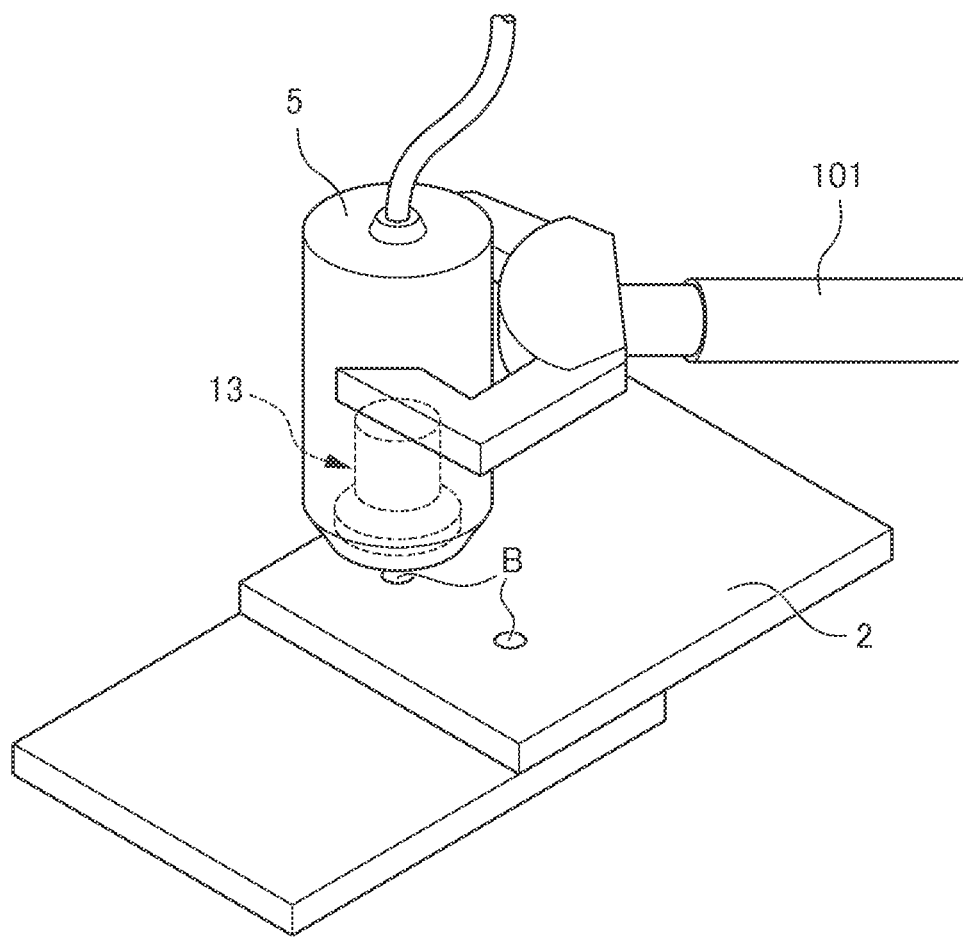
FIG. 5 is a view offering an explanation for a method of attaching a sensor probe to a robot arm and measuring a measurement subject.

Herein, a method will be explained of attaching a sensor probe 5 including the magnetic core 13, exciting coil 14 and induced electromotive force detector 17 to a robot arm 101 (arm portion) as shown in FIG. 5, causing to move over the measurement subject 2, and then estimating the center location of the nugget and diameter of the nugget. It should be noted that the robot arm 101 is connected to a control device (drive control unit) not illustrated, and is configured to be able to freely move over the measurement subject 2, in accordance with the control of the control device. In addition, the leading end of the robot arm 101 is configured to be able to rotate in the horizontal direction, in accordance with the control of the control device.

The sensor probe 5 is arranged at a predetermined location (for example, welding dent B in FIG. 5) over the measurement subject 2 by way of the robot arm 101. It should be noted that the sensor probe 5 may contact the measurement subject 2, or may be arranged at a place a predetermined height from the measurement subject 2.

The sensor probe 5 performs the first measurement in order to test the inner structure at the predetermined location.

Then, when the first measurement is finished, the robot arm 101 rotates the leading end part by a predetermined angle (for example, 90°) in the horizontal direction.

Next, the sensor probe 5 performs the second measurement in order to test the inner structure at a location rotated by a predetermined angle.

The processor 20 calculates the center location of the nugget formed inside of the measurement subject 2 and the diameter of the nugget, based on the inner structure detected by the first measurement and the inner structure detected by the second measurement.

Case of Microcoils being Arranged Length and Width Wise in Cross Shape

Next, the induced electromotive force detector 17 may be configured by a plurality of the microcoils arranged in one vertical line and one horizontal line in a cross shape. When configured in this way, the processor 20 arranges the induced electromotive force detector 17 at a predetermined location on the measurement subject 2, performs the first measurement by way of the induced electromotive force detector 17 arranged in one vertical line or one horizontal line, and subsequently performs the second measurement by way of the induced electromotive force detector 17 arranged in one horizontal line or one vertical line.

Herein, the core shape of the magnetic core 13 and the configuration of the induced electromotive force detector 17 will be explained using FIG. 6 for a case of the microcoils being arranged length and width wise in a cross shape.

Figure 6:
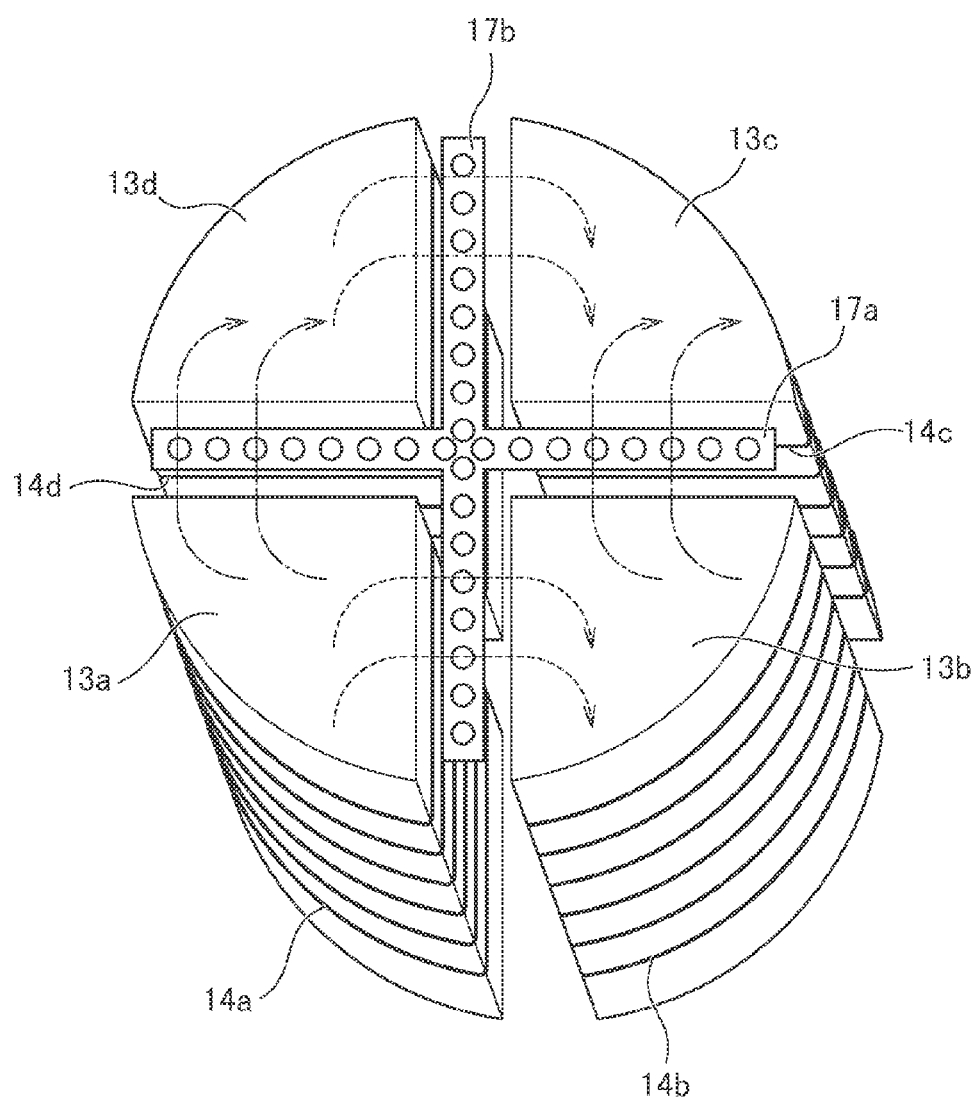
FIG. 6 is a view schematically showing the configuration of a magnetic core and induced electromotive force detector in a case of a microcoils being disposed length and width wise in a cross shape.

The induced electromotive force detector 17 has a first detector 17a and second detector 17b, in which a plurality of coils are arranged uniformly, that are configured in a cross shape, as shown in FIG. 6.

The magnetic core 13 is configured by small magnetic cores 13a, 13b, 13c and 13d. The small magnetic cores 13a, 13b, 13c and 13d are respectively wound around the circumference in a predetermined direction according to exciting coils 14a, 14b, 14c and 14d. In addition, the small magnetic cores 13a, 13b, 13c and 13d are respectively arranged in each region of the induced electromotive force detector 17 configured in a cross shape, as shown in FIG. 6. It should be noted that, since the small magnetic core 13c acts as a common pole in the present example, the exciting coil 14c does not need to be wound.

Next, the method of measuring the measurement subject by way of the non-destructive testing device 1 configured in this way will be explained.

The sensor probe 5 is arranged at a predetermined location (for example, welding dent) over the measurement subject 2 by way of the robot arm 101. It should be noted that the sensor probe 5 may contact the measurement subject 2, or may be arranged at a place a predetermined height from the measurement subject 2.

The sensor probe 5 performs the first measurement in order to test the inner structure at the predetermined location. The sensor probe 5, for example, in the first measurement, causes a magnetic flux to be generated between the small magnetic core 13a and small magnetic core 13d and between the small magnetic core 13b and small magnetic core 13c, applying a magnetic field to the welded area 3, and after the elapse of a predetermined time period, discontinues the magnetic flux, and detects the change in magnetic flux occurring at the welded area 3 by way of the first detector 17a.

In addition, when the first measurement finishes, the sensor probe 5 remains at this location and performs the second measurement in order to test the inner structure. The sensor probe 5, for example, in the second measurement, causes a magnetic flux to be generated between the small magnetic core 13a and small magnetic core 13b and between the small magnetic coil 13d and small magnetic coil 13c, applying a magnetic field to the welded area 3, and after the elapse of a predetermined time period, discontinues the magnetic flux, and detects the change in magnetic flux occurring at the welded area 3 by way of the second detector 17b.

The processor 20 calculates the center location of the nugget formed inside of the measurement subject 2 and the diameter of the nugget, based on the inner structure detected by the first measurement and the inner structure detected by the second measurement.

Measurement Principle

Next, the measurement principle by the non-destructive testing device 1 will be explained. Magnetic flux leaving the exciting coil 14 (excitation pole 11) for generating magnetism passes through the induced electromotive force detector 17 arranged directly below the exciting coil 14, enters into the measurement subject 2 (workpiece), passes through the nugget, and returns back to the original exciting coil 14 (excitation pole 11) through the common pole 12.

Herein, if focusing on the coils C configuring the array coil, letting the surface area of the coil C be S, the length of the magnetic path be L, and the magnetic permeability be $\mu$, the magnetic resistance Rm is calculated by $Rm = L/S \times \mu$. In regards to the appearance when applying a magnetic field to cause a magnetic flux density to be generated (the details will be described later using FIG. 12A and FIG. 12B), the magnetic field is slowly produced, and before long becomes direct current. Then, when the magnetism is reduced by discontinuing the magnetic field at a predetermined timing, a waveform of $e = -d\Phi/dt$ appears in the coils C, comparing with the change in magnetic flux density (refer to FIG. 12A described later). In addition, it is possible to estimate the magnetic resistance of the magnetic flux passing through each coil, by integrating the change in magnetic flux density generated in all of the coils C1 to C16 and obtaining a segment of the curve represented by an exponential function and a time constant. When obtaining the magnetic resistance of each coil, performing smoothing processing, and displaying on a display, it is possible to schematically visualize the inner structure of the measurement subject 2.

In addition, the factors influencing the magnetic resistance can be generally classified into the three of form (air space), residual stress and hardness.

Figure 7:
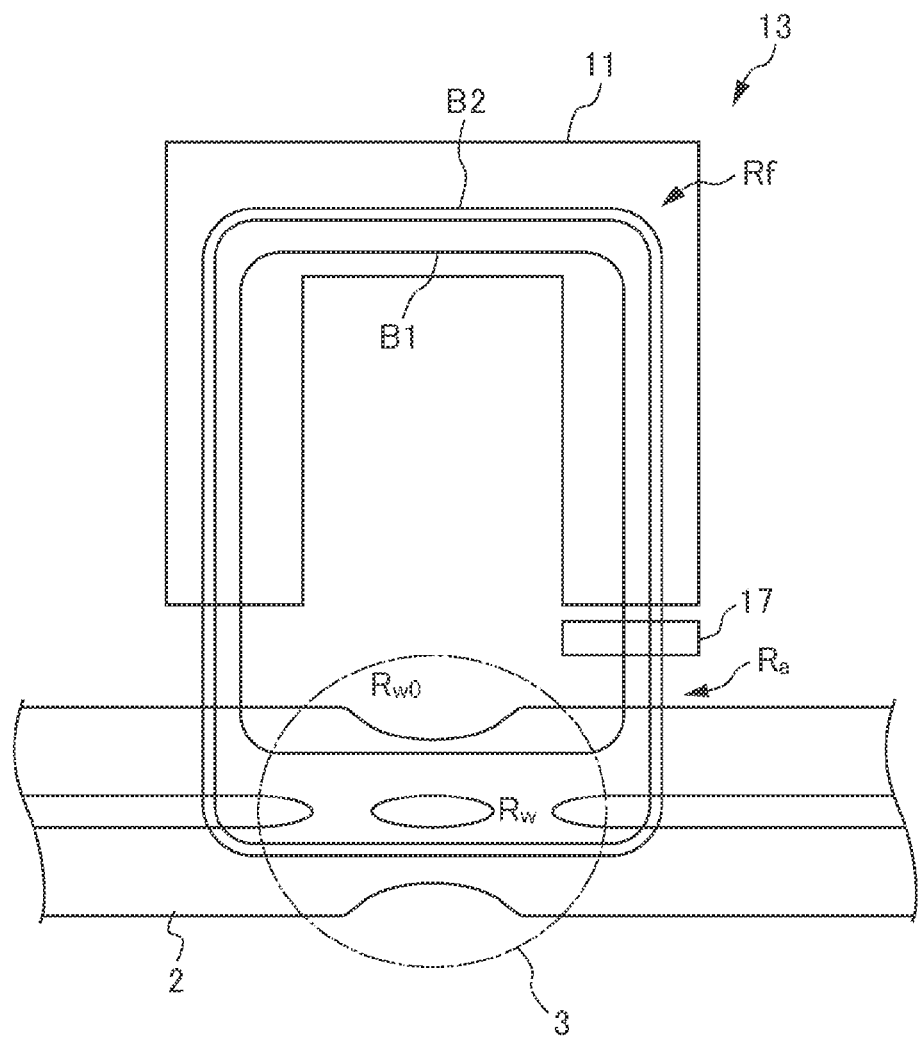
FIG. 7 is a view offering an explanation for when applying a magnetic field in two stages to a workpiece.

As shown in FIG. 7, the magnetic flux generated by the exciting coil 14 enters inside of the measurement subject 2 (workpiece) by passing through the vacant space via the induced electromotive force detector 17. Subsequently, the magnetic flux comes to be influenced by the residual stress and hardness inside of the workpiece.

Herein, as shown in FIG. 7, the non-destructive testing device 1 causes twice magnetic fields to be generated in the workpiece by way of the exciting coil 14. More specifically, as a first magnetic field, the exciting coil 14 causes a magnetic field density to be generated that is a magnetic field application of a short time by applying a shallow magnetic field into the workpiece by way of the skin effect (B1 in FIG. 7). In addition, as a second magnetic field, the exciting coil 14 causes a magnetic flux density to be generated that is a magnetic field application of a sufficiently long time by applying a deep magnetic field into the workpiece until arriving at the nugget (B2 in FIG. 7).

Then, the processor 20 acquires a differential magnetic resistance R between the measurement result (magnetic resistance $R_0$) obtained by causing the magnetic flux density to be generated by applying a shallow magnetic field, and the measurement result (magnetic resistance $R_2$) obtained by causing the magnetic flux density to be generated by applying a deep magnetic field.

$$R_0 = R_f + R_a + R_{w0}$$

$$R_2 = R_f + R_a + R_w$$

$$R = R_2 - R_0 = R_w - R_{w0}$$

It should be noted that $R_f$ indicates the magnetic resistance possessed by the sensor itself configured from the magnetic core 13 and induced electromotive force detector 17, and Ra indicates the magnetic resistance existing between the workpiece and sensor. In addition, $R_{wO}$ indicates the magnetic resistance of the workpiece surface, and $R_w$ indicates the magnetic resistance inside of the workpiece.

Therefore, the differential magnetic resistance R is the resistance value in which the magnetic resistance $R_f$ possessed by the sensor itself and the magnetic resistance $R_a$ existing between the workpiece and the sensor have been removed (canceled). The non-destructive testing device 1 can obtain a precise magnetic resistance R without being influenced by the surface shape of the workpiece, due to obtaining the differential magnetic resistance R from the measurement results of two stages in this way.

It should be noted that, in the foregoing, the non-destructive testing device 1 measures the magnetic resistance $R_O$ by causing a magnetic flux density to be generated by applying a shallow magnetic field at first, and subsequently measuring the magnetic resistance $R_2$ by causing a magnetic flux density to be generated by applying a deep magnetic field; however, it is not limited thereto, and may measure the magnetic resistance $R_2$ by causing a magnetic flux density to be generated by applying a deep magnetic field at first, and subsequently measuring the magnetic resistance $R_0$ by causing a magnetic flux density to be generated by applying a shallow magnetic field.

Time Constant Calculation Method

Next, a specific method of calculating the decay time constant $\tau_1$ of the magnetic energy and the decay time constant $\tau_2$ of the eddy current loss by way of the processor 20 will be explained. The coils C1 to C16 of the non-destructive testing device 1 are arranged at the top surface of a part of the measurement subject 2 serving as the test target. Then, the non-destructive testing device 1 establishes the exciting coil 14 in the energized state, and causes a magnetic flux density to be generated by applying a magnetic field to the measurement subject 2 by way of the magnetic flux generated between the excitation pole 11 and the common pole 12. Herein, a schematic appearance when causing the magnetic flux density to be generated by applying a magnetic field is shown in FIG. 8A. As shown in FIG. 8A, a magnetic field is applied at a magnetic flux passage portion of the measurement subject 2, and a magnetic flux density generates in accordance with the strength of the magnetic field.

In addition, in the case of the exciting coil 14 of the non-destructive testing device 1 being established in the isolated state, the loop of magnetic flux separates into a closed loop in the vicinity of the exciting coil 14 and a closed loop in the vicinity of the measurement subject 2 (refer to FIG. 8B). The closed loop of magnetic flux in the vicinity of the exciting coil 14 rapidly decreases and disappears. On the other hand, the closed loop of the magnetic flux in the vicinity of the measurement subject 2 does not immediately disappear (remnant magnetism) and is maintained in the magnetic body as a magnetic energy, and gradually disappears to finally return to a state before static magnetic field application.

The non-destructive testing device 1 detects the change in the magnetic flux of the measurement subject 2 with respect to time by way of the coils C1 to C16. The change in magnetic flux detected by the coils C1 to C16 after the static magnetic field is discontinued ideally monotonously decreases exponentially; however, since there is loss in actual practice, it decreases to depict a predetermined curve.

Figure 9A:
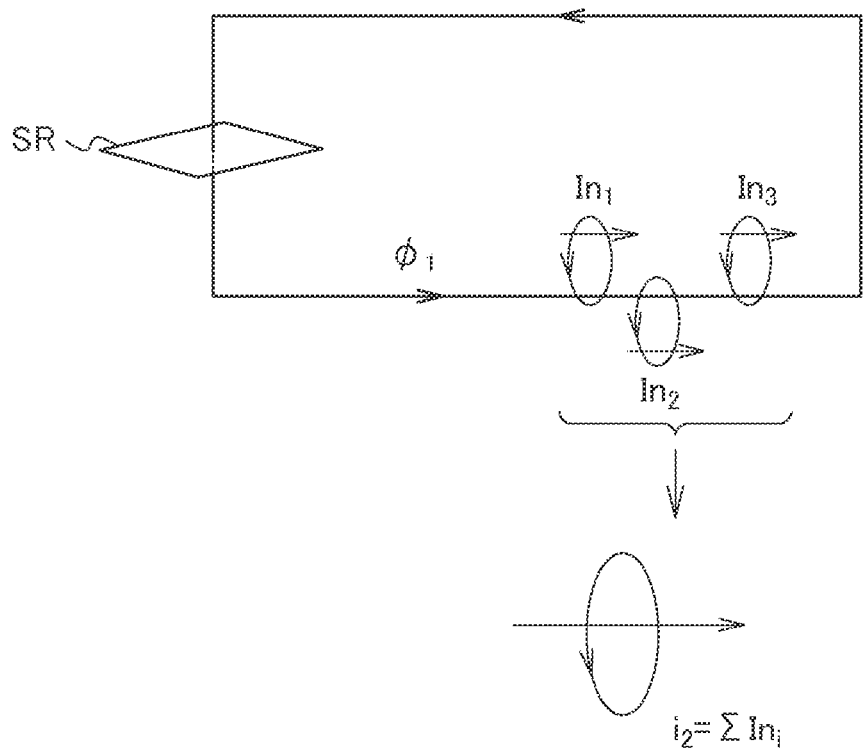
FIG. 9A and FIG. 9B provides views schematically showing the loss process of remnant magnetism.
Figure 9B:
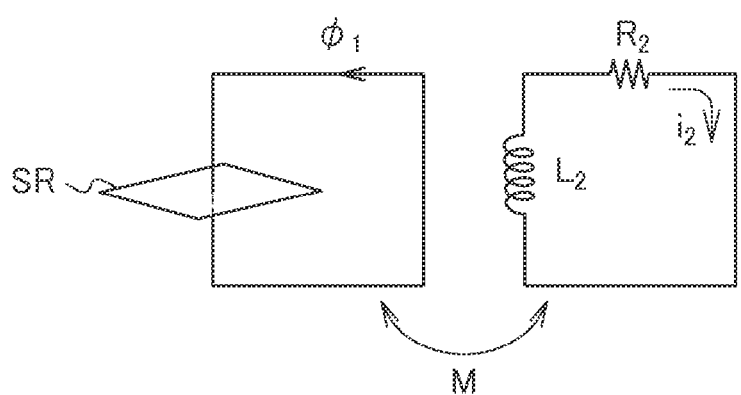

FIG. 9A and FIG. 9B shows the loss process of the remnant magnetism. As shown in FIG. 9A, in this magnetic energy loss process, the magnetic flux density passing through any one of the coils C1 to C16 is defined as $\phi_1$. In addition, the eddy current induced by the change in the magnetic flux density $\phi_1$ is defined as $In_1, In_2, In_3 \ldots$, and the coefficients of electrostatic induction of these are respectively defined as $M_1, M_2, M_3 \ldots$. The eddy currents $In_1, In_2, In_3 \ldots$ induced from the change in magnetic flux density $\phi_1$ are considered to each be independent. At this time, the eddy currents $In_1, In_2, In_3 \ldots$ can be replaced by the eddy current $i_2$ of one induced by the coefficient of electrostatic induction $M = \Sigma Mi$ ($i=1, 2, 3, \ldots$) depending on the change in magnetic flux density $\phi_1$. In other words, the loss process of magnetic flux passing through any one of the coils C1 to C16 can be represented by the magnetic flux density $\phi_1$ and the eddy current $i_2$ induced by the coefficient of electrostatic induction $M$ from the magnetic flux density $\phi_1$. FIG. 9B shows an equivalent circuit to FIG. 9A. Herein, $R_2$ indicates the electrical resistance of the eddy current $i_2$, and $L_2$ indicates the inductance of the eddy current $i_2$.

Figure 10:
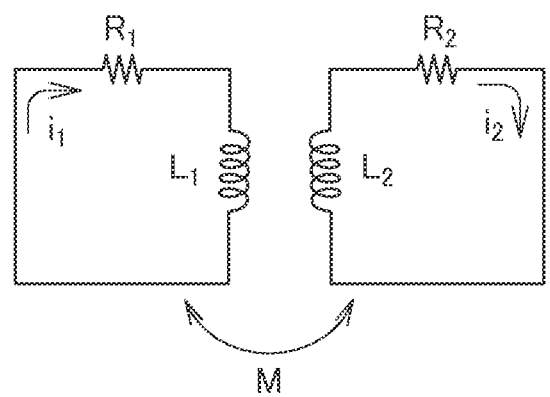
FIG. 10 is a view showing a circuit diagram made by substituting the closed loop of magnetic flux density shown in FIG. 9B with a magnetism equivalent circuit.

FIG. 10 was prepared by replacing the closed loop of the magnetic flux density $\phi$ with a magnetic equivalent circuit. Herein, $i_1$ indicates magnetic flux density, $R_1$ indicates the recovery difficulty (resistance) of the magnetic flux at the measured site retaining magnetic flux, $L_1$ indicates the inductance of the magnetic flux space retaining magnetic flux, $i_2$ indicates the eddy current of the measured site, $R_2$ indicates the electrical resistance of the eddy current loop, and $L_2$ indicates the volume of the space in which the eddy current generates.

Figure 11:
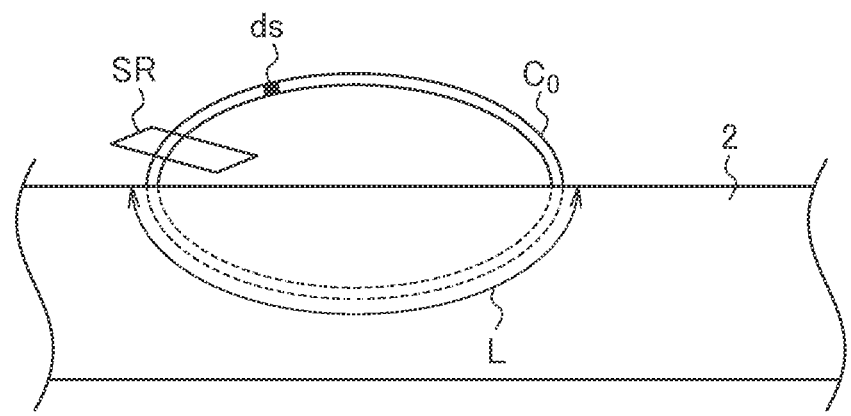
FIG. 11 is a view schematically showing a closed loop $C_0$ of magnetic flux passing through any one array sensor immediately after discontinuing a static magnetic field.

FIG. 11 shows a closed loop $C_O$ of a magnetic flux $i_1$ ($=\phi_1$) passing through any one of the coils C1 to C16 immediately after discontinuing the static magnetic field. At this time, the magnetic energy stored during static magnetic field application does not immediately disappear, but rather gradually disappears. This magnetic energy is retained in the space of the closed loop of the magnetic flux, and is considered to gradually disappear due to the recovery difficulty of the magnetic flux applied in the space. The magnetic energy $W$ can be represented by formula (8). It should be noted that $L$ in FIG. 11 indicates the length of the magnetic flux density generated by the magnetic field being applied.

[Math. 4]

$$W = \frac{1}{2\mu}\int i_1^2 dv = \frac{1}{2}L i_1^2 \tag{8}$$

Herein, $L$ is a value proportional with the volume of the space retaining the magnetic flux (i.e. space retaining magnetic energy). On the other hand, formula (8) is the same formula as the energy accumulated when the current $i_1$ flows in a coil of inductance $L$. Based on these facts, the inductance $L_1$ in FIG. 10 is understood to correspond to the volume of the entire space retaining magnetic flux.

In addition, when the equivalent circuit shown in FIG. 10 is represented in a formula, it is written as formulas (9a) and (9b).

[Math. 5]

$$L_1 \frac{di_1}{dt} + R_1 i_1 - M \frac{di_2}{dt} = 0 \tag{9a}$$

$$L_2 \frac{di_2}{dt} + R_2 i_2 - M \frac{di_1}{dt} = 0 \tag{9b}$$

When solving formulas (9a) and (9b), the formulas (10a) and (10b) are obtained.

[Math. 6]

$$i_1 = A_1 \exp(-(\alpha - \gamma)t) - A_2 \exp(-(\alpha + \gamma)t) \tag{10a}$$

$$i_2 = B_1 \exp(-(\alpha - \gamma)t) - B_2 \exp(-(\alpha + \gamma)t) \tag{10b}$$

$$\alpha = \frac{L_1 R_2 + L_2 R_1}{2(L_1 L_2 - M^2)}$$

$$\gamma = \frac{\sqrt{(L_1 R_2 - L_2 R_1)^2 - 4 R_1 R_2 M^2}}{2(L_1 L_2 - M^2)}$$

$$A_1 = \frac{-(L_1 R_2 - L_2 R_1) - \sqrt{(L_1 R_2 - L_2 R_1)^2 + 4 R_1 R_2 M^2}}{2 R_1 \sqrt{(L_1 R_2 - L_2 R_1)^2 + 4 R_1 R_2 M^2}}$$

$$A_2 = \frac{(L_1 R_2 - L_2 R_1) - \sqrt{(L_1 R_2 - L_2 R_1)^2 + 4 R_1 R_2 M^2}}{2 R_1 \sqrt{(L_1 R_2 - L_2 R_1)^2 + 4 R_1 R_2 M^2}}$$

$$B_1 = \frac{-M}{\sqrt{(L_1 R_2 - L_2 R_1)^2 + 4 R_1 R_2 M^2}}$$

$$B_2 = B_1$$

Herein, as the initial conditions, the magnetic flux density $i_1$ when the static magnetic field is discontinued (t=0) is defined as $I_0$, and establishes a constant in formulas (10a) and (10b). At this time, in the case of the coefficient of electrostatic induction $M$ being small and the eddy current $i_2$ induced from the change in magnetic flux density $i_1$ being small, i.e. when defined as $L1 \cdot L2 \gg M \cdot M$, the following results are obtained.

[Math. 7]

$$\alpha - \gamma \approx \frac{R_1}{L_1} = \frac{1}{\tau_1} \tag{11a}$$

$$\alpha + \gamma \approx \frac{R_2}{L_2} = \frac{1}{\tau_2} \tag{11b}$$

$$A_1 \approx I_0 \approx -\frac{1}{R_1} \tag{11c}$$

$$A_2 \approx 0 \tag{11d}$$

$$B_1 \approx 0 \tag{11e}$$

$$B_2 \approx 0 \tag{11f}$$

When formulas (11a) and (11b) are substituted into formula (10a), the following formula (12) is obtained.

[Math. 8]

$$i_1 = A_1\exp\left(-\frac{t}{\tau_1}\right) - A_2\exp\left(-\frac{t}{\tau_2}\right) \quad (12)$$

Figure 12A:
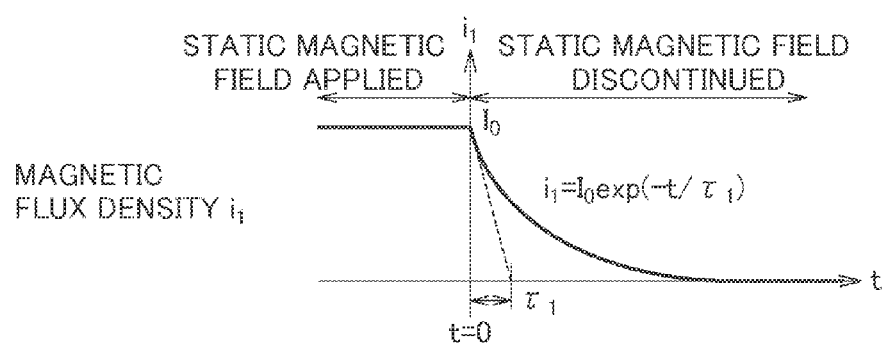
FIG. 12A and FIG. 12B provides graphs offering an explanation for the change in magnetic flux measured by the array sensor.

A value that can be actually measured is the magnetic flux density $i_1$ on the left side of formula (12). FIG. 12A shows the transient change in the magnetic flux density $i_1$ obtained by formula (12). Herein, as is evident from formula (4d), the second term on the right side of formula (12) can be ignored, and can be approximated with only the first term. On the other hand, the voltage measured by a loop coil generally used as a magnetism sensor is a value proportional to the rate of change in the magnetic flux density, i.e. differential magnetic flux density. Therefore, formula (12) is differentiated with time t to obtain a formula of differential magnetic flux density expressed by formula (13).

$$\frac{di_1}{dt} = -\frac{A_1}{\tau_1}\exp\left(-\frac{t}{\tau_1}\right) + \frac{A_2}{\tau_2}\exp\left(-\frac{t}{\tau_2}\right) \quad \text{[Math. 9]}$$

$$= -\frac{A_1}{\tau_1}\left(\exp\left(-\frac{t}{\tau_1}\right) - \frac{A_2\tau_1}{A_1\tau_2}\exp\left(-\frac{t}{\tau_2}\right)\right)$$

Provided when $$t = 0, \frac{di_1}{dt} = 0 \rightarrow \frac{\tau_1 A_2}{A_1 \tau_2} = 1$$

$$\frac{di_1}{dt} = -\frac{A_1}{\tau_1}\left(\exp\left(-\frac{t}{\tau_1}\right) - \exp\left(-\frac{t}{\tau_2}\right)\right)$$

Provided when $A_1 \approx I_0$ $$\frac{di_1}{dt} = -\frac{I_0}{\tau_1}\left(\exp\left(-\frac{t}{\tau_1}\right) - \exp\left(-\frac{t}{\tau_2}\right)\right) \quad (13)$$

Figure 12B:
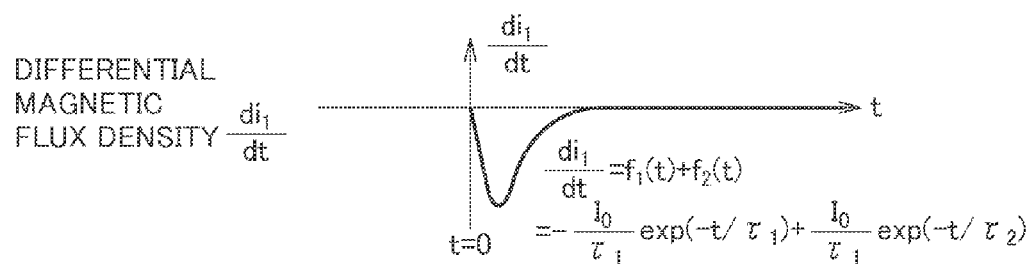

FIG. 12B shows the transient change in differential magnetic flux density obtained by formula (13). Formula (12) is a formula expressing the change in magnetic flux density $i_1$ obtained by the coils C1 to C16, and formula (13) is a formula expressing the change in differential magnetic flux density ($di_1/dt$).

Herein, the time constant $\tau_1$ of the first term on the right side of formula (13) equals "L1/R1", as is obtained by formula (11a). In addition, the first term on the right side of formula (13) is a term expressing the attenuation characteristic of the magnetic flux density, i.e. decay property of the magnetic energy, in the vicinity of the measurement subject 2 after the static magnetic field is discontinued. In the spot welded part, a change occurs in this time constant $\tau_1$ between the nugget (portion at which a change in metal composition or structural strength occurs) and a portion other than the nugget (portion at which a change in metal composition or structural strength does not occur). Therefore, if the distribution of the time constant $\tau_1$ in the spot welded part is measured, and this is analyzed, the shape and dimensions of the portion in which a composition change occurs metallically as in the nugget can be obtained.

In addition, the time constant $\tau_2$ of the second term on the right side of formula (13) equals "L2/R2", as is obtained by formula (11b). Therefore, this term corresponds to the time constant of an equivalent circuit of the eddy current $i_2$ shown in FIG. 10. In other words, the second term on the right side of formula (13) is a term expressing the decay property of the eddy current loss. As shown in FIG. 11, when the length of the magnetic flux density inside of the measurement subject 2 is defined as L and the magnetic flux passage area is defined as ds, it is possible to express $L_2$ by formula (14).

[Math. 10]

$$L_2 \propto \int dv = 1 \cdot ds \quad (14)$$

Therefore, from formulas (11b) and (14), the time constant $\tau_2$ of the decay property of the eddy current loss is proportional to the length of the magnetic path in which the eddy current generates, i.e. magnetic path passing through the steel sheet, as shown in formula (15).

[Math. 11]

$$\tau_2 \propto 1 \quad (15)$$

In other words, the change in the length of the magnetic path of the magnetic flux passing through the vicinity of the spot welded part can be detected as the change in the time constant $\tau_2$ of the decay property of the second term on the right side of formula (13).

As shown by the aforementioned measurement principle, the non-destructive testing device 1 calculates the time constant arrived at by canceling the magnetic resistance $R_f$ possessed by the sensor itself and the magnetic resistance $R_a$ existing between the workpiece and sensor, based on the time constant when causing magnetic flux density to be generated by applying a shallow magnetic field and the time constant when causing a magnetic flux density to be generated by applying a deep magnetic field, and substitutes the time constant of the coil detecting an air space as the time constant of coils arranged in axially symmetric locations. Therefore, even if a part of the coils detects an air space, it is possible to perform testing smoothly without inhibiting testing work, and not influencing the detection results of other coils.

Other Examples

In addition, the non-destructive testing device 1 may be a configuration other than the aforementioned example.

As another example of the non-destructive testing device 1, a configuration is proposed in which a first induced electromotive force detector 17c and a second induced electromotive force detector 17d are arranged in parallel so as to be able to measure a nugget that is within range of a magnetosphere, by allowing a magnetic field generated from one excitation pole 11 to be recovered without loss in common poles 12a, 12b arranged on the right and left.

In addition, by configuring in this way, the non-destructive testing device 1 uses the two of the first induced electromotive force detector 17c and the second induced electromotive force detector 17d; therefore, when compared with the device configured by one induced electromotive force detector, it is possible to realize twice the measurement precision, and the ease of measurement can be improved.

In addition, the non-destructive testing device 1 can obtain not linear (one-dimensional), but rather planar (two-dimensional) or steric (three-dimensional) measurement results, and thus a more multifaceted measurement of nugget is possible.

In addition, the non-destructive testing device 1 additionally has the following such merits.

Since the measurement method (measuring by approaching or contacting a sensor probe 5 with a welding dent) is simple, mastery is easy.

The sensor probe 5 does not need to be rotated during measurement.

A circuit such as for switching is unnecessary.

The nugget diameter can be estimated from measurement one time.

The resolution improves.

The directionality of a line of magnetic force can be improved.

In addition, the specific configuration will be explained below.

As mentioned above, the processor 20 causes a magnetic flux density to be generated by applying a magnetic field to the measurement subject 2, measures magnetic flux emitted from a plurality of locations on the measurement subject 2 by way of the induced electromotive force detector 17 after the magnetic field is discontinued, calculates a plurality of time constants of transient change in the magnetic flux, and detects the internal structure of the measurement subject 2 from the distribution state of the time constants.

In addition, with the common pole 12 provided in parallel in the longitudinal direction of the excitation pole 11 (excitation part) on both sides thereof, and a plurality of the induced electromotive force detectors 17 being arranged below the excitation pole 11 so as to correspond to the common poles 12, the processor 20 measures the magnetic flux emitted from a plurality of locations on the measurement subject 2 by way of the plurality of induced electromotive force detectors 17, and based on the results of this measurement, estimates the center location of the nugget formed inside of the measurement subject 2 and/or the diameter of the nugget.

Figure 13A:
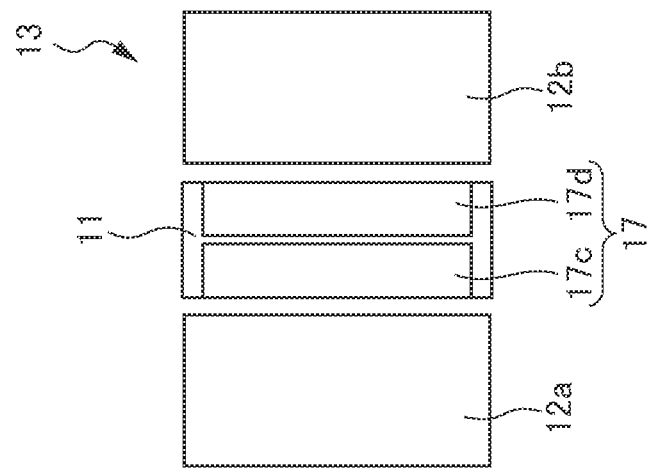
FIG. 13A and FIG. 13B provides views schematically showing the configuration of the magnetic core and induced electromotive force detector.
Figure 13B:
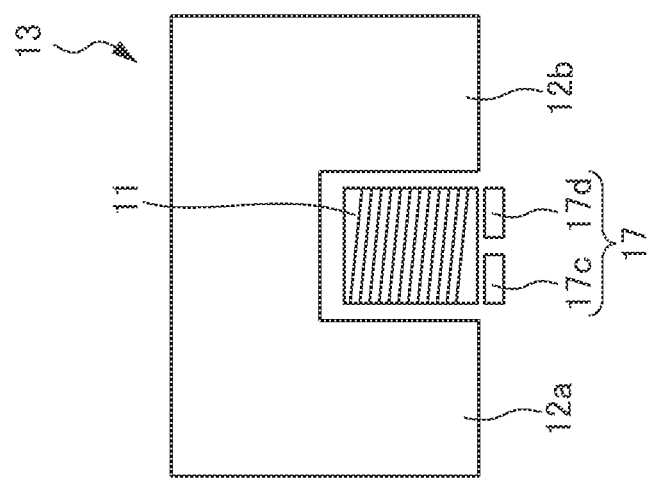

Herein, the shape of the magnetic core 13 will be explained. FIG. 13A shows an exterior view when viewing the magnetic core 13 from a frontal direction, and FIG. 13B shows an exterior view when viewing the magnetic core 13 from a bottom direction.

The magnetic core 13 is configured by forming the common poles 12a, 12b in a U-shape, and arranging the excitation pole 11 in the space portion formed in the U-shape, as shown in FIG. 13A. In addition, the induced electromotive force detector 17 is arranged under the excitation pole 11 so as to correspond to the common poles 12a, 12b. It should be noted that the induced electromotive force detector 17 has a plurality of microcoils arranged in axial symmetry as shown in FIG. 2.

In addition, the induced electromotive force detector 17 is configured from a first induced electromotive force detector 17c and a second induced electromotive force detector 17d.

The first induced electromotive force detector 17c is arranged under the excitation pole 11 in parallel to one common pole 12a.

The second induced electromotive force detector 17d is arranged below the excitation pole 11 in parallel to the other common pole 12b.

Figures 14A, 14B:
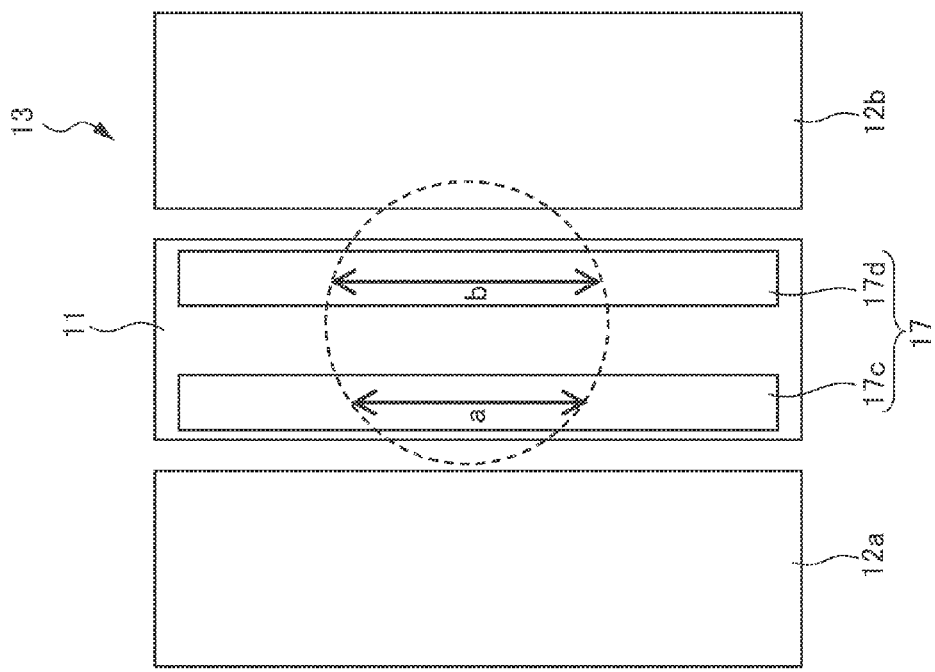
FIG. 14A and FIG. 14B provides views offering an explanation for the flow of processing when estimating the diameter of a nugget.

In addition, the processor 20 acquires measurement results of the first induced electromotive force detector 17c and the second induced electromotive force detector 17d. More specifically, the processor 20 analyzes the distribution of respective decay time constants of the magnetic energy from the detection results of the first induced electromotive force detector 17c and the second induced electromotive force detector 17d, and calculates a line segment a and a line segment b as shown in FIG. 14A. It should be noted that the length of the line segment a is calculated according to the number of coils detecting the nugget, among the plurality of coils constituting the first induced electromotive force detector 17c. Similarly, the length of the line segment b is calculated according to the number of coils detecting the nugget, among the plurality of coils constituting the second induced electromotive force detector 17d.

The processor 20 forms a triangle by extracting from the measurement results the three points most separated. In the example shown in FIG. 14B, a triangle is formed from the starting point or ending point of the line segment a and the starting point and ending point of the line segment b.

The processor 20 forms a circumscribed circle c passing through the three points, from the intersection of perpendicular bisectors on the triangle arrived at by respectively calculating perpendicular bisectors of two sides forming the triangle.

Then, the processor 20 estimates the center location of the nugget formed inside of the measurement subject 2 and/or diameter of the nugget, by calculating the center location d and diameter e of the circumscribed circle c.

In addition, the non-destructive testing device 1 can virtually draw an estimated nugget and display on a display unit 23. A display controller 22 generates a virtual image of the nugget, in a case of having estimated the center location of a nugget formed inside of the measurement subject 2 and/or diameter of the nugget, based on the center location and/or diameter of the nugget, and displays the virtual image on the display unit 23.

More specifically, the processor 20 scans the sensor probe 5 containing the magnetic core 13 over the measurement subject 2, as shown in FIG. 15A, FIG. 15B and FIG. 15C, and performs measurement at a plurality of places (in the example shown in FIG. 15A, FIG. 15B and FIG. 15C, three places).

It should be noted that FIG. 15A shows the exterior view when measuring (first measurement) by causing the sensor probe to approach a position to the left from the center location of the welding dent. FIG. 15B shows an exterior view when measuring (second measurement) by causing the sensor probe 5 to approach the center location of the welding dent. FIG. 15C shows an exterior view when measuring (third measurement) by causing the sensor probe 5 to approach a position to the right from the center location of the welding dent.

In addition, the processor 20 analyzes the distribution of decay time constants of the magnetic energy obtained from the first induced electromotive force detector 17c and the second induced electromotive force detector 17d by way of the first measurement, and calculates a magnetic waveform (FIG. 15D). The processor 20 calculates the line segment a and the line segment b from the magnetic waveform thus calculated. The lengths of the line segment a and the line segment b are calculated according to the number of coils detecting the nugget, among the plurality of coils constituting the first induced electromotive force detector 17c and second induced electromotive force detector 17d. In addition, the processor 20 calculates a circle c1 forming intersections with the starting points of and ending points of the line segment a and line segment b, as shown in FIG. 15G, and estimates this as the diameter of the nugget.

Furthermore, the processor 20 analyzes the distribution of decay time constants of the magnetic energy obtained from the first induced electromotive force detector 17c and second induced electromotive force detector 17d by way of the second measurement, and calculates the magnetic waveform (FIG. 15E). The processor 20 calculates a line segment c and line segment d from the magnetic waveform thus calculated. The lengths of the line segment c and line segment d are calculated according to the number of coils detecting the nugget, among the plurality of coils constituting the first induced electromotive force detector 17c and second induced electromotive force detector 17*d*. In addition, the processor 20 calculates a circle c2 forming intersections with the starting points and ending points of the line segment c and line segment d as shown in FIG. 15H, and estimates this as the diameter of the nugget.

Furthermore, the processor 20 analyzes the distribution of decay time constants of the magnetic energy obtained from the first induced electromotive force detector 17*c* and second induced electromotive force detector 17*d* by way of the third measurement, and calculates the magnetic waveform (FIG. 15F). The processor 20 calculates a line segment e and line segment f from the magnetic waveform thus calculated. The lengths of the line segment e and line segment f are calculated according to the number of coils detecting the nugget, among the plurality of coils constituting the first induced electromotive force detector 17*c* and second induced electromotive force detector 17*d*. In addition, the processor 20 calculates a circle c3 forming intersections with the starting points and ending points of the line segment e and line segment f as shown in FIG. 15I, and estimates this as the diameter of the nugget.

The display controller 22 generates a planar image based on the circles c1 to c3 calculated by the processor 20, and displays as a virtual image (planar) of the nugget on the display unit 23 (FIG. 15J). It should be noted that, in the present example, the line segment b and line segment e are measured at the same place, and thus are displayed overlapping.

In addition, the display controller 22 generates a three-dimensional image based on the circles c1 to c3 calculated by the processor 20, and displays as a virtual image (three-dimensional) of the nugget on the display unit 23 (FIG. 15K). It should be noted that, in the present example, the line segment b and line segment e are measured at the same place, and thus are displayed overlapping. In addition, the display controller 22 calculates the height of the nugget, based on the height of the magnetic waveform calculated from the first measurement, second measurement and third measurement.

In this way, the non-destructive testing device 1 displays a virtual image of a nugget planarly or three-dimensionally on the display unit 23, based on the results measured at a plurality of locations, and thus can allow for visual understanding of the shape and size of the nugget, and can improve the precision of testing.

The invention claimed is:

1. A non-destructive testing device, comprising:
a magnetic flux generator having an excitation controller, and
a detection processor, which are adapted to generate a magnetic flux density by applying a magnetic field to a measurement subject,
said testing device further comprising a magnetic flux detection element,
said detection processor further adapted to:
measure magnetic flux emitted from a plurality of locations on the measurement subject by way of the magnetic flux detection element,
calculate, after the magnetic field is discontinued, a plurality of time constants of transient change in magnetic flux, and
detect an internal structure of the measurement subject from a distribution state of the time constants,
wherein the magnetic flux detection element comprises a plurality of microcoils arranged in a vertical line and a horizontal line, the lines forming a cross shape,
wherein the detection processor is adapted
to dispose the magnetic flux detection element at a predetermined location on the measurement subject,
to performs a first measurement using a first subset of microcoils of the plurality of microcoils arranged in the vertical line, and
to perform a second measurement by way of a second subset of microcoils of the plurality of microcoils arranged in the horizontal line at the same location as the predetermined location, and
wherein the detection processor is adapted to estimate a center location of a nugget formed inside of the measurement subject and/or diameter of the nugget,
by calculating an intersection between: a perpendicular line passing through a central point of a connecting line of first two points extracted, by acquiring measurement results from the first measurement, and extracting from the measurement results the first two points of corresponding to two microcoils of the first subset of microcoils, the first two points corresponding to a contour line of the nugget; and
a perpendicular line passing through a central point of a connecting line of second two points extracted, by acquiring measurement results from the second measurement, and extracting from the measurement results the second two points corresponding to two microcoils of the second subset of microcoils, the second two points corresponding to the contour line of the nugget;
setting the intersection thus calculated as a center location, and calculating a diameter of a circle passing through the first two points or the second two points centering around the center location.

2. The non-destructive testing device according to claim 1, further comprising:
an arm portion that holds a measurement device having the magnetic flux detection element; and
a drive controller adapted to move the arm portion so that the magnetic flux detection element is arranged at a predetermined location on the measurement subject serving as a measurement target.

3. The non-destructive testing device according to claim 1, further comprising:
a display unit; and
a display controller adapted to control the display unit,
wherein the display controller is adapted to generate a virtual image of the nugget based on the center location and/or diameter of the nugget, in a case of the center location of the nugget formed inside of the measurement subject and/or the diameter of the nugget having been estimated, and to display the virtual image on the display unit.

4. The non-destructive testing device according to claim 1, wherein the detection processor is further adapted to estimate the diameter of the nugget by calculating an average of the diameter of the circle passing through the two points of the one vertical line and the diameter of the circle passing through the two points of the one horizontal line.

5. The non-destructive testing device according to claim 4, further comprising:
an arm portion that holds a measurement device having the magnetic flux detection element; and
a drive controller adapted to move the arm portion so that the magnetic flux detection element is arranged at a predetermined location on the measurement subject serving as a measurement target.

6. The non-destructive testing device according to claims 4, further comprising:
a display unit; and
a display controller adapted to control the display unit,
wherein the display controller is adapted to generate a virtual image of the nugget based on the center location and/or diameter of the nugget, in a case of the center location of the nugget formed inside of the measurement subject and/or the diameter of the nugget having been estimated, and to display the virtual image on the display unit.

7. A non-destructive testing device, comprising:
a magnetic flux generator having an excitation controller, and
a detection processor which are adapted to cause a magnetic flux density to be generated by applying a magnetic field to a measurement subject, said testing device further comprising a magnetic flux detection element,
said detection processor being adapted to measure magnetic flux emitted from a plurality of locations on the measurement subject by way of the magnetic flux detection element, said detection processor further being adapted to calculate, after the magnetic field is discontinued, a plurality of time constants of transient change in magnetic flux, and to detect an internal structure of the measurement subject from a distribution state of the time constants:,
wherein the magnetic flux generator comprises a magnetic core composed of magnetic recovery portions and an excitation portion,
wherein the magnetic recovery portions are provided in a longitudinal direction of the excitation portion in parallel on both sides thereof,
wherein the magnetic flux detection element comprises a first magnetic flux detection element and a second magnetic flux detection element,
wherein the first magnetic flux detection element is arranged below the excitation portion in parallel to one magnetic recovery portion,
wherein the second magnetic flux detection element is arranged below the excitation portion in parallel to another magnetic recovery portion,
wherein the detection processor is adapted to acquire measurement results of the first magnetic flux detection element and the second magnetic flux detection element, to form a triangle by extracting from the measurement results three points that are the most distant and correspond to a contour line of a nugget, to form a circumscribed circle passing through the three points from an intersection of perpendicular bisectors on the triangle arrived at by respectively calculating perpendicular bisectors of two sides forming the triangle, to calculate a center location and diameter of the circumscribed circle, and thereby to estimate a center location of the nugget formed inside of the measurement subject and/or a diameter of the nugget, and
wherein the extracted three points represent the starting and ending point of a line segment, the line segment having a length calculated according to the number of coils detecting the nugget.

8. The non-destructive testing device according to claim 7, further comprising:
an arm portion that holds a measurement device having the magnetic flux detection element; and
a drive controller adapted to move the arm portion so that the magnetic flux detection element is arranged at a predetermined location on the measurement subject serving as a measurement target.

9. The non-destructive testing device according to claim 7, further comprising:
a display unit; and
a display controller adapted to control the display unit,
wherein the display controller is adapted to generate a virtual image of the nugget based on the center location and/or diameter of the nugget, in a case of the center location of the nugget formed inside of the measurement subject and/or the diameter of the nugget having been estimated, and to display the virtual image on the display unit.

\* \* \* \* \*